United States Patent [19]
Koto et al.

[11] 3,994,986
[45] Nov. 30, 1976

[54] METHOD OF PRODUCING CYCLOPENTENE

[75] Inventors: Yasushi Koto; Masakazu Uekita; Shoichi Matsumura; Yoshiaki Taguchi; Yutaka Takanoo, all of Kobe, Japan

[73] Assignee: Kanegafuchi Kagaku Kogyo Kabushiki Kaisha, Osaka, Japan

[22] Filed: Apr. 14, 1975

[21] Appl. No.: 567,835

[30] Foreign Application Priority Data
Apr. 13, 1974 Japan............................. 49-41889

[52] U.S. Cl. .................... 260/666 A; 260/666 DQ; 260/666 P
[51] Int. Cl.² .......................................... C07C 3/00
[58] Field of Search ........... 260/666 A, 666 P, 667, 260/666 D

[56] References Cited
UNITED STATES PATENTS

| | | | |
|---|---|---|---|
| 2,349,047 | 5/1944 | Lycan et al. ................... | 260/666 A |
| 2,453,044 | 11/1948 | Staff................................ | 260/666 A |
| 3,565,963 | 2/1971 | Tabler et al. ................... | 260/666 D |
| 3,598,877 | 8/1971 | Fountain et al................. | 260/666 D |
| 3,715,404 | 2/1973 | Lindlar et al. .................. | 260/666 A |
| 3,751,497 | 8/1973 | Schwerdtel et al. ............ | 260/666 A |
| 3,751,499 | 8/1973 | Tazuma et al. ................. | 260/666 A |
| 3,763,254 | 10/1973 | Engelhard et al............... | 260/666 A |
| 3,793,381 | 2/1974 | Kohler et al..................... | 260/666 P |

*Primary Examiner*—Veronica O'Keefe
*Attorney, Agent, or Firm*—Moonray Kojima

[57] ABSTRACT

A method of producing cyclopentene comprising the steps of depolymerizing dicyclopentadiene to produce raw cyclopentadiene; feeding the raw cyclopentadiene to a distillation tower having an upper part cooled to a temperature near the boiling point of the cyclopentadiene and an outlet maintained at 35° to 60° C and a lower part at a temperature of 40° to 150° C; thereby to produce highly pure gaseous cyclopentadiene at the top outlet and impure components having high boiling point at the lower outlet which are removed continuously; mixing the highly pure cyclopentadiene obtained thereby with hydrogen and reacting in a first hydrogenation reactor using a palladium containing catalyst, then mixing the resulting product with hydrogen and reacting in a second hydrogenation reactor with a palladium containing catalyst; cooling the resulting product and separating the liquid phase from the gas phase and recirculating the gas phase for use in the hydrogenation reactions.

5 Claims, 1 Drawing Figure

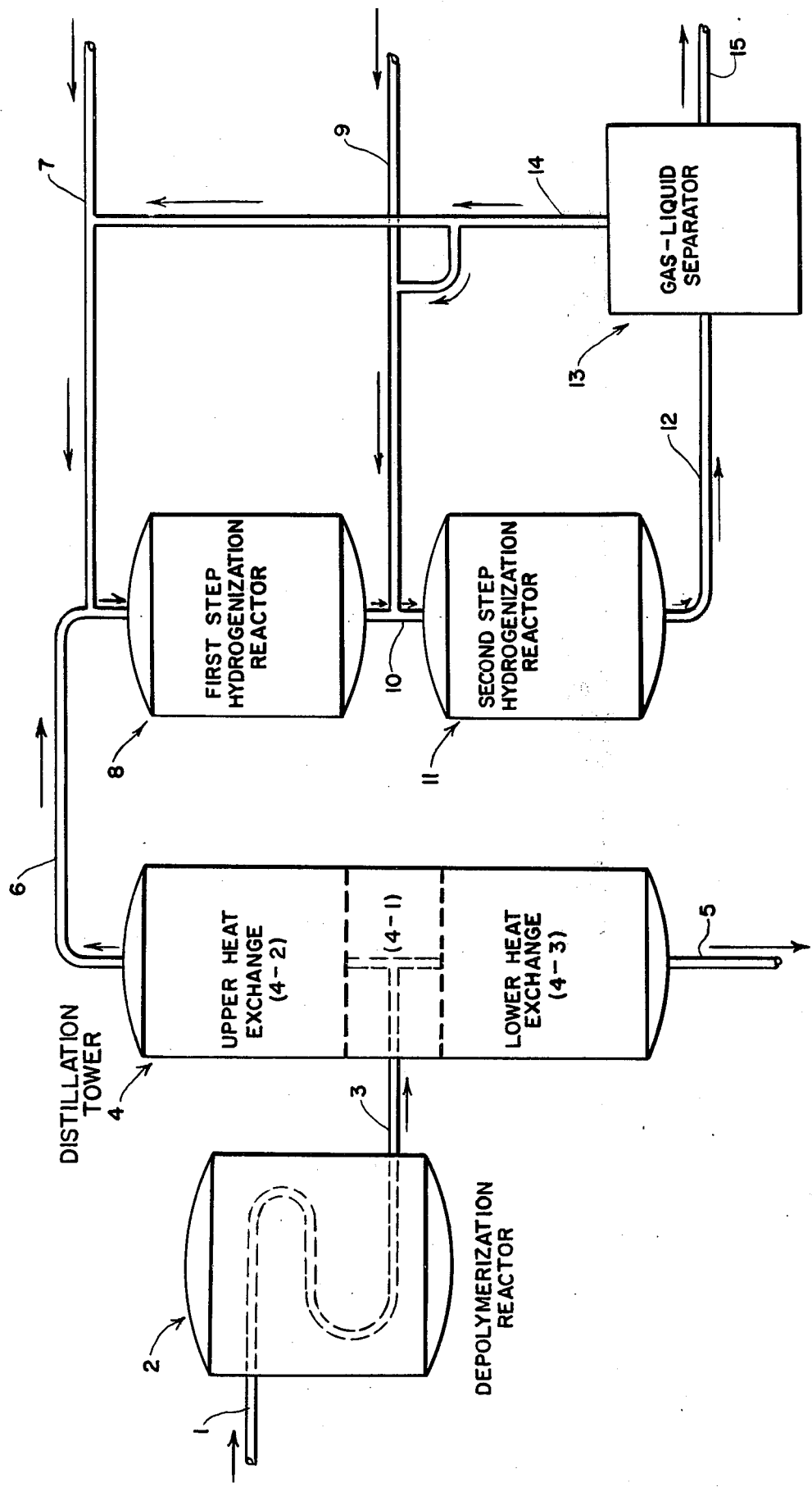

METHOD OF PRODUCING CYCLOPENTENE

BACKGROUND OF THE INVENTION

The present invention relates to a method of producing cyclopentene.

Cyclopentene is useful for example, as a raw material for producing cyclic aldehydes, alcohols and chlorinated compounds, and also as fuel. Recently cyclopentene has been used as a monomer which is polymerized to a high molecular weight polymer. However, the amount of cyclopentene available on the commercial market is so small and the cost thereof is so expensive that use thereof in industrial quantities is unrealistic. There are other reasons for its lack of widespread industrial use. For example, there have been many difficulties encountered in the production of cyclopentene such as during thermal depolymerization of dicyclopentadiene, during selective hydrogenation of cyclopentadiene monomer and during purification of hydrogenated cyclopentene. There is yet no known method which combines these processes into a smooth and economical procedure to produce substantially pure cyclopentene from dicyclopentadiene.

To combine thermal decomposition of dicyclopentadiene and hydrogenation of cyclopentadiene, many problems arise due to the thermal instability of cyclopentadiene monomer. Accordingly, after thermal decomposition of dicyclopentadiene, it is necessary to send the diene monomer to a hydrogenation zone as soon as possible after a quick purification of the monomer. Moreover to prevent dimerization of the monomer, it is necessary to prevent exposure thereof to pressure or to heat before the hydrogenation.

One of the important problems to be solved in the hydrogenation of cyclopentadiene is the decrease of catalytic activity and concurrent decrease of catalytic life time by the adsorption of impurities of high boiling point contained in cyclopentadiene, such as dicyclopentadiene, co-dimers of cyclopentadiene and isoprene or pentadiene, etc.

SUMMARY OF THE INVENTION

An object of the invention is to eliminate the deficiencies and disadvantages of the prior art methods.

Another object of the invention is to provide a process which combines the depolymerization of dicyclopentadiene and purification of the cyclopentadiene produced thereby and the hydrogenation in at least one step thereby to produce a highly pure cyclopentene.

A further object of the invention is to reduce the unwanted reduction of catalytic activity and life time resulting from the presence of unwanted impurities in the cyclopentadiene.

The foregoing and other objects of the invention are attained in a method of producing cyclopentene, comprising the steps of feeding raw dicyclopentadiene to a thermal reactor for depolymerization at 170° to 400° C, preferably 250° to 350° C, and at substantially ordinary atmospheric pressure, into cyclopentadiene; then feeding the raw cyclopentadiene to the middle part of a distillation tower having an upper part at 30° to 80° C with an upper outlet at the top thereof at 35° to 60° C, preferably at 35° to 45° C, and a lower part at 40° to 150° C, thereby to produce highly pure, over 99%, cyclopentadiene in gaseous form through the upper outlet, and at the lower part outlet higher boiling point components which are continuously drained off; and then, feeding the highly pure cyclopentadiene to a first hydrogenation chamber wherein hydrogen gas is reacted therewith in the ratio of 1 to 2 mol, preferably 1 to 1.5, mol hydrogen per 1 mol of cyclopentadiene, in the presence of a palladium containing catalyst thereby to produce a conversion rate of 90 to 98%; and thereafter feeding the unreacted cyclopentadiene to a second hydrogenation chamber wherein 1 to 20, preferably 1 to 7, mol of hydrogen is employed per mol of unreacted cyclopentadiene in the presence of a palladium containing catalyst, and thereafter cooling the resulting product, separating the liquid and gas portions and recirculating the gas portion for use in the hydrogenation steps. The hydrogenation reaction temperature is 50° to 200° C, preferably, 70° to 180° C, in substantially ordinary atmospheric pressure.

A feature of the invention is the use of a distillation tower having an upper part at 30° to 80° C with an upper outlet at 35° to 60° C, preferably 35° to 45° C, and a lower part at 40° to 150° C, to purify raw cyclopentadiene by supplying same to the midpoint between the upper and lower parts and having high boiling point impurities removed continuously from the lower part and removing gaseous high purity cyclopentadiene from the upper outlet after fractionating in the tower.

A further feature of the invention is the use of the purified cyclopentadiene as raw material for use in hydrogenation with hydrogen in a mol ratio of 1 to 2 mol, preferably 1 to 1.5 mol, hydrogen to 1 mol cyclopentadiene in a first hydrogenation reactor at 50° to 200° C, preferably 70° to 180° C, and at substantially ordinary atmospheric pressure in the presence of a palladium containing catalyst.

Another feature of the invention is the use of a second hydrogenation reactor immediately after the first hydrogenation reactor wherein unreacted cyclopentadiene is reacted with hydrogen mixed in the ratio of 1 to 20, preferably 1 to 7, mol of hydrogen and 1 mole of unreacted cyclopentadiene in the presence of a palladium containing catalyst, and the subsequent cooling of the resulting product and the separation of the liquid and gas parts with the gaseous part being recirculated for use in the first and second hydrogenation reactors.

Another feature is the use of a palladium containing catalyst carried on alumina, silica or magnesium oxide together with use of iron or chromium.

BRIEF DESCRIPTION OF DRAWING

The single FIGURE depicts an illustrative apparatus in which the method of the invention may be practiced.

DETAILED DESCRIPTION OF PREFERRED EMBODIMENTS

After extensive study, the inventors have discovered a method of removing substantially all impurities of high boiling point from the raw cyclopentadiene obtained from decomposing dicyclopentadiene, and then supplying same for hydrogenation using a palladium containing catalyst. In other words, the present invention encompasses a method of producing cyclopentene combining two subprocesses, one involving purifying cyclopentadiene obtained from thermal decomposition or depolymerization of dicyclopentadiene, and another involving the hydrogenation reaction of the purified cyclopentadiene by mixing with hydrogen and reacting in the presence of a palladium containing catalyst.

The invention can be better understood with reference to the drawing in which raw material containing a substantial portion of raw dicyclopentadiene may be supplied through pipe or inlet 1, into a depolymerization or thermal decomposition reactor 2, thereby to decompose or depolymerize the dicyclopentadiene into raw cyclopentadiene containing various impurities, such as unreacted dicyclopentadiene, co-dimer of cyclopenten, etc, which have a high boiling point. The reactor is maintained at 170° to 400° C, preferably 250°–350° C, and at substantially ordinary atmospheric or slightly higher pressure. The raw dicyclopentadiene is in gaseous state. The raw cyclopentadiene produced by the depolymerization or decomposition is gaseous and contains the above mentioned impurities, and is fed through pipe 3, which cools the gas somewhat, into the midpoint 4-1 of distillation tower 4. The tower 4 comprises an upper heat exchanger 4-2 and a lower heat exchanger 4-3 and an inlet at the midpoint between the upper and lower portions 4-1, and also the tower has an upper outlet (not labeled) connected to pipe 6 and a lower outlet (not labeled) connected to pipe 5. The upper part 4-2 may be filled with packing material and is rapidly cooled to a temperature of 30° to 80° C. The upper outlet is maintained at 35° to 60° C, more preferably 35° to 45° C. The lower part may be filled with packing material and is maintained at 40° to 150° C. The distillation tower acts upon the raw cyclopentadiene to separate the high boiling point impurities from the cyclopentadiene. The high boiling point impurities or components are fractionated in the distillation tower 4 and is removed continuously from the lower outlet 5. The gaseous cyclopentadiene is removed continuously from the upper outlet 6, and is passed through pipe 6 and is then mixed with a controlled stream of hydrogen gas passing through pipe 7. The ratio of hydrogen to purified cyclopentadiene at this stage is 1 to 2, preferably 1 to 1.5 mol hydrogen per mol of cyclopentadiene. The mixture is then supplied to reactor 8 to be selectively hydrogenated in the presence of a palladium containing catalyst. The hydrogenation reactor 8 is at 50° to 200° C, preferably 70° to 180° C, and at atmospheric pressure or slightly higher. A conversion rate of 90 to 98% cyclopentene from the highly purified cyclopentadiene was obtained.

The reaction product from reactor 8 is then again mixed at junction 10 with a controlled stream of hydrogen gas passing through pipe 9 in the ratio of 1 to 20, preferably 1 to 7, mol of hydrogen to one mol of unreacted cyclopentadiene and the unreacted cyclopentadiene contained in the reaction product coming from reactor 8, is then selectively hydrogenated in the second hydrogenation reactor 11, using a palladium containing catalyst. The reactor 11 is at 50° to 200° C, preferably 70° to 180° C, and at ordinary atmospheric pressure or slightly higher.

Although shown herein to be mixed prior to hydrogenation reaction in reactors 8 and 11, the mixing can be done within the reactors. Also, in place of the second hydrogenation reactor 11, the reaction product of reactor 8, may be once liquified by cooling and then separated into gaseous and liquid parts by a knock out pot. The liquid portion may then be sent to an evaporator using a dosing pump and the evaporated gas may be mixed with a controlled stream of hydrogen gas through pipes 9 and then introduced to the second hydrogenation reactor 11.

The catalyst used in the hydrogenation reactions is a palladium containing catalyst, carried, for example on alumina, silica or magnesium oxide and used together with iron, chromium, etc. The same or different catalysts may be used in the different hydrogenation reactors 8 and 11.

The reaction product from reactor 11 contains only a minute amount of cyclopentadiene monomer, about less than several hundred parts per million (ppm). It is cooled down by passing through a cooling pipe 12 and then separated into two phases, gas and liquid, by a knock out pot 13. The separated gases are sent via pipes 14 and are recycled through pipes 7 and 9 for use in the first and second hydrogenation reactions. The liquid portion containing the purified cyclopentene passes through an outlet 15 and may be stored or sent to a further distillation process for further use or treatment.

As the distillation tower for fractionating of the raw material, although it is possible to use any type of distillation tower, it is preferable to use one comprising an upper heat exchanger filled with packing material and maintained at 30° to 80° C at the outside, and situated at the upper side of an inlet used to feed in the raw cyclopentadiene having impurities therein, and a lower heat heat exchanger located below the inlet and filled with packing material and maintained at 40° to 150° C at the outside. The cyclopentadiene is introduced in a gaseous state. The upper outlet is maintained at 35° to 60° C, and more preferably 35° to 45° C. Thus, the raw cyclopentadiene having various other impurities is reacted to separate the impurities from the cyclopentadiene. The impurities have high boiling point and are direct to the lower outlet where such impurities are continuously removed. The purified gaseous cyclopentadiene is taken out continuously from the top outlet. In this manner a cyclopentadiene monomer of high purity, in the range over 99% is obtained in gaseous state.

Comparing the 99% purity to that degree of purity obtained by prior art methods will distinctly show that by use of the invention an unexpected result was obtained. In U.S. Pat. No. 2,913,504, a distillation column of 30 plates was used. The inlet temperature of raw cyclopentadiene was 150° C with the temperature at the top of the tower being 38° to 42° C, the reflux ratio being 3.5 and the temperature of reboiler being 143° C. A purified cyclopentadiene monomer was produced of a purity of 95.2 to 97.8%. As will be discussed hereinafter impurities of, for example 4.8 to 2.2%, as present in the prior art cyclopentadienes, will adversely affect the catalytic activity and lifetime of the catalyst when used in the production of cyclopentene by hydrogenation of the impurities containing cyclopentadiene. On the other hand, the present invention produces impurities of less than 1%, which extra degree of purity makes possible industrial use of the process which would not have been previously possible.

This unexpected purity of cyclopentadiene which is produced by the rectifying tower of the present invention results, it is thought, from first, retaining the cyclopentadiene in the tower for a relatively short time, by rapid elimination of excess heat of raw material by maintaining the temperature of the upper portion heat exchanger at 30° to 80° C and by effectively maintaining the temperature of the cyclopentadiene at a desired temperature; and second, the retaining of the high boiling point components for a relatively short time by removing it continuously from the bottom of the tower by providing a heat exchanger at the lower side of the inlet and maintaining its temperature at a temperature higher than the boiling point of cyclopentadiene monomer but lower than the boiling point of the impurities such as dicyclopentadiene, such as within the range of 40° to 150° C.

When cyclopentadiene is partially hydrogenated to produce cyclopentene, it inevitably contains several percent of cyclopentadiene remaining unreacted therein. However, in case cyclopentene is used as a monomer to produce, for example, trans-polypentenamer, which is a polymer becoming more important industrially, the content of cyclopentadiene in cyclopentene should be less than several hundred ppm, since the existence of diolefine, especially such as cyclopentadiene, disturbs smooth polymerization reaction of cyclopentene.

There are known various processes for purification of raw cyclopentene, such as distillation, dimerization, treatment with maleic acid anhydride, adsorption method, ion exchange method and hydrogenation method. The method involving dimerization of cyclopentadiene to dicyclopentadiene is deficient in that it is impossible to remove cyclopentadiene completely since there exists a chemical equilibrium between the monomer and the dimer. The method involving treatment with maleic acid anhydride is also deficient in that the acid remains in the purified cyclopentene in a small amount. The adsorption method or the ion exchange method, such as disclosed in U.S. Pat. No. 3,506,732 wherein an adsorbent of zinc oxide-silica-alumina system is used, or Japanese Pat. No. 4963/1972 wherein an ion exchanger of basic property is used, are deficient in that it is necessary to use a large amount of absorbent or ion exchanger, compared with the amount of cyclopentadiene to be removed and moreover there is the problem of reactivating these materials.

Also in the art, U.S. Pat. No. 3,565,963, for example, discloses a method of hydrogenating cyclopentadiene in two stages in the presence of a nickel catalyst to obtain cyclopentene. The method is deficient in that the nickel catalyst is poisoned by sulfur and thus requires further treatment. Moreover the method's hydrogenation reaction is carried out at a high temperature under pressure.

The inventors solved such difficulties as mentioned above by the two stage hydrogenation of cyclopentadiene in the presence of palladium containing catalyst, as set forth hereinabove.

As the raw material used for conversion to cyclopentadiene, a dicyclopentadiene whose purity is about 95% may be used in the present invention and even if the purity of dicyclopentadiene to be used is lower than this, such as 80 to 95%, it is sufficient for the method of the present invention to add the inventive distillation apparatus to obtain a cyclopentene of sufficiently high purity for polymerization use.

In producing cyclopentene from dicyclopentadiene, various problems arise due to the thermal instability of cyclopentadiene monomer. The inventive method carries out the entire process in the gaseous system, thus eliminating these problems, since cyclopentadiene monomer is relatively stable in the gaseous form. Moreover, the inventors have simplified the industrial plant needed to work the process. The inventive method has produced an unexpectedly low content of unreacted cyclopentadiene in cyclopentene, to an amount of less than several hundred ppm.

Thus, the present invention has overcome difficulties and deficiencies which previously prevented large-scale industrial production of cyclopentene from dicyclopentadiene, and moreover, the invention has provided a simiplified process. To summarize some of the difficulties and deficiencies of the prior art, which have been overcome by the invention: (1) It was necessary to purify cyclopentadiene rapidly due to its thermal instability. (2) It was necessary to prevent the dimerization or further polymerization of cyclopentadiene by protecting it from heating or compressing after thermal decomposition of dicyclopentadiene and use of a short retention time. (4) The selective activity of catalyst for hydrogenation must be increased to prevent the formation of saturated compound, that is, cyclopentene, and the removal of cyclopentadiene contained in cyclopentene as an impurity when the cyclopentene was used as a monomer for production of polymers. (5) It was necessary to remove impurities of high boiling point, such as dicyclopentadiene, co-dimers of cyclopentadiene, etc., which shorten the life and retard the catalytic activity of catalysts for hydrogenation. By resolving the foregoing problems, the present invention has made an important contribution to the art.

The invention will be further illustrated by an actual example, which is for illustrative purposes and is not to be construed to be limiting.

EXAMPLE

As the thermal depolymerization apparatus 2, a tubular type reactor comprising four tubes connected to each other was used. Each tube had a heating jacket with a heating medium and an inner diameter of 21.6 mm $\phi$, and a length of 1 m. When it was desired to have packing material, such was packed only in the last one meter. The obtained results are shown in Table 1.

TABLE 1

| Feed Rate of Raw Material (purity 95%) (kg/hr) | Jacket Temperature (° C) | Degree of Decomposition (%) | Packing Material |
|---|---|---|---|
| 2.0 | 310 | 91.6 | none |
| 2.0 | 310 | 96.7 | filled |

As the distillation tower 4, there was used one comprising an upper heat exchanger 4-2 situated at the upper side of inlet 4-1 into which the raw material comprising cyclopentadiene was fed, and having pipes whose dimension were 2 cm of diameter and 30 cm of length, filled with packing material, and maintained at 50° C of outside temperature, and a lower heat exchanger 4-3 situated at the lower side of inlet 4-1, having 7 pipes whose dimensions were 2 cm diameter and 30 cm length, filled with packing material and maintained at 100° C of outside temperature. The high boiler component fractionated in the tower was continuously removed from the bottom 5 of the tower. The raw material cyclopentadiene obtained from the depolymerization reactor 2 was introduced continuously in a gaseous state. The obtained results are shown in Table 2.

TABLE 2

| Feed Amount at inlet (kg/hr) | High boiling point component at inlet (%) | Cyclopentadiene at inlet (%) | High Boiling point component at top outlet (%) | Cyclopentadiene at top outlet (%) | Amount removed from bottom (kg/hr) |
| --- | --- | --- | --- | --- | --- |
| 2.0 | 8.4 | 90.9 | 0.2 | 99.0 | 0.3 |
| 2.0 | 3.3 | 95.9 | 0.1 | 99.1 | 0.2 |

As the hydrogenation reaction vessels 8, 11, a heat exchanger type reactor comprising 20 tubes whose dimensions were 1.8 cm diameter, was used. The outside temperature was 120° C. The amount of catalyst used was 25 ml at the first step of hydrogenation and 17 ml at the second step of hydrogenation, such amount being for each reaction tube. The reaction times of gas were 1.0 sec and 1.3 sec respectively. The results are shown in Table 3.

TABLE 3

First step of hydrogenation

| Feed at inlet (kg/hr) | $H_2$/cyclopentadiene | Cyclopentane (%) | Cyclopentene (%) | Cyclopentadiene (%) | High Boiling Pt. components, and other $C_5$, $C_6$ impurities (%) |
| --- | --- | --- | --- | --- | --- |
| 1.8 | 1.1 | 4.6 | 90.0 | 4.4 | 1.0 |

Second step of hydrogenation

| $H_2$/cyclopentadiene | Cyclopentane (%) | Cyclopentene (%) | Cyclopentadiene (%) | High Boiling Pt. components, and other $C_5$, $C_6$ impurities (%) |
| --- | --- | --- | --- | --- |
| 2.4 | 5.4 | 93.6 | 130 | 1.0 |
| 3.0 | 6.0 | 93.0 | 70 | 1.0 |

The catalysts used in the Example were prepared by the following method. After immersing a magnesium oxide whose surface area was 1 m²/g, into a 3.5% aqueous solution of hydrochloric acid containing palladium chloride and ferrous chloride, reduction of metallic ions contained in the magnesium oxide was carried out for 2 hours using an aqueous solution containing 10% hydrazine and 10% caustic soda and the product was washed with water until the chloride ion did not exist in the filtrate and dried at 150° C for 12 hours in a vacuum dryer. The obtained catalyst carried on magnesium oxide contained 0.48% palladium and 0.32% iron.

COMPARATIVE EXAMPLE

In the first step of hydrogenation, a cyclopentadiene whose purity was 95.2% and which had 4.0% of high boiling point components, was used as raw material. The experimental results are shown below in Table 4, using the above conditions. The life time of the catalyst was also decreased to 12 hours.

TABLE 4

| Feed at inlet (kg/hr) | $H_2$/cyclopentadiene | Cyclopentane (%) | Cyclopentene (%) | Cyclopentadiene (%) | High Boiling Pt. component and other $C_5$, $C_6$, impurities (%) |
| --- | --- | --- | --- | --- | --- |
| 1.8 | 1.1 | 9.0 | 77.1 | 9.1 | 4.8 |

The foregoing description is for purposes of illustrating the principles of the invention. Numerous other variations and modifications thereof would be apparent to the worker skilled in the art. All such variations and modifications are to be considered to be within the spirit and scope of the invention.

What is claimed is:

1. A method of producing cyclopentene, comprising the steps of
   A. thermal decomposition or depolymerization of dicyclopentadiene in a gaseous state at 170 to 400° C and at substantially ordinary atmospheric pressure to produce cyclopentadiene and other high boiling point impurities;
   B. feeding the raw cyclopentadiene and impurities produced in step (A) into a two part distillation tower, the upper part being maintained at 30° to 80° C and the lower part maintained at 40° to 150° C and an outlet located at the top of said tower being maintained at 35° to 60° C, whereby cyclopentadiene having a purity of 99% or more is continuously removed from said top outlet, and said high boiling point impurities are removed continuously from a lower part outlet of said tower;
   C. reacting the purified cyclopentadiene of step (B) with hydrogen gas in the ratio of 1 to 1.5 mol hydrogen to 1 mol cyclopentadiene, in the presence of a palladium catalyst on a carrier and at a temperature of 50° to 200° C and at substantially ordinary atmospheric pressure thereby to produce a conversion ratio of 90 to 98% cyclopentene, remainder unreacted cyclopentadiene;
   D. reacting the unreacted cyclopentadiene of step (C) with hydrogen gas in the mol ratio of 1 to 7 mol hydrogen to 1 mole of unreacted cyclopentadiene, in the presence of a palladium containing catalyst, at a temperature of 50° to 200° C and at substantially ordinary atmospheric pressure, thereby to produce cyclopentene; and
   E. cooling the resulting product of step (D), and separating the liquid part from the gaseous part and recirculating the gaseous part to steps (C) and (D) above.

2. The method of claim 1, wherein said depolymerization or decomposition temperature is 250° to 350° C; the temperature of the upper outlet is 35° to 45° C; and the temperature of hydrogenation reaction of steps (C) and (D) is 70° to 180° C.

3. The method of claim 1, wherein said palladium containing catalyst comprises palladium and iron or chromium carried on a carrier of alumina, silica or magnesium oxide.

4. Process of purifying cyclopentadiene comprising the steps of feeding raw gaseous material containing cyclopentadiene and impurities of high boiling point to the middle part of a distilling tower having an upper heat exchanger, an upper outlet, a middle part, a lower heat exchanger, and a lower outlet, said upper heat exchanger maintained at 30° to 80° C, said upper outlet maintained at 35° to 60° C, and said lower heat exchanger maintained at 40 to 150° C, whereby substantially pure cyclopentadiene of over 99% purity is removed continuously from said upper outlet in gaseous form, and said higher boiling point impurities is removed continuously from said lower outlet.

5. The process of claim 4, wherein said upper outlet is maintained at 35° to 45° C.

* * * * *